United States Patent
Auweter et al.

(10) Patent No.: US 6,863,914 B1
(45) Date of Patent: *Mar. 8, 2005

(54) STABLE, AQUEOUS DISPERSIONS AND STABLE, WATER-DISPERSIBLE DRY POWDERS OF XANTHOPHYLLS, AND PRODUCTION AND USE OF THE SAME

(75) Inventors: Helmut Auweter, Limburgerhof (DE); Heribert Bohn, Wattenheim (DE); Erik Lüddecke, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,351

(22) PCT Filed: Apr. 17, 2000

(86) PCT No.: PCT/EP00/03467

§ 371 (c)(1),
(2), (4) Date: Oct. 24, 2001

(87) PCT Pub. No.: WO00/66665

PCT Pub. Date: Nov. 9, 2000

(30) Foreign Application Priority Data

Apr. 29, 1999 (DE) .......................... 199 19 751

(51) Int. Cl.$^7$ .......................... A23L 1/275; C09B 61/00
(52) U.S. Cl. .................... 426/250; 426/599; 426/540; 426/654; 424/490
(58) Field of Search ................... 426/250, 599, 426/540, 654; 424/490

(56) References Cited

U.S. PATENT DOCUMENTS

| | | | |
|---|---|---|---|
| 3,110,598 A | | 11/1963 | Mueller |
| 4,522,743 A | | 6/1985 | Horn et al. |
| 5,364,563 A | | 11/1994 | Cathrein |
| 6,007,856 A | * | 12/1999 | Cox et al. .................. 426/250 |
| 6,261,598 B1 | * | 7/2001 | Runge et al. ............... 424/456 |
| 6,296,877 B1 | * | 10/2001 | Auweter et al. ............ 424/490 |
| 6,509,029 B2 | * | 1/2003 | Runge et al. ............... 424/439 |

FOREIGN PATENT DOCUMENTS

| | | |
|---|---|---|
| CA | 1330270 | 6/1994 |
| DE | 1 211 911 | 3/1966 |
| DE | 196 51681 | 6/1998 |
| EP | 065 193 | 11/1982 |
| EP | 278 284 | 8/1988 |
| EP | 410 236 | 1/1991 |
| GB | 918399 | 2/1963 |
| WO | 91/06292 | 5/1991 |
| WO | 94/19411 | 9/1994 |
| WO | WO 98/26008 | * 6/1998 |
| WO | 98/26008 | 6/1998 |

OTHER PUBLICATIONS

Chimia 21, 329–335, Manz.
Biochem. Photo B: Biol, 21 (1993) 229–234, Ruban et al.
Photochemistry and Photobiology, 1974, vol. 19, pp 435–441, Song et al.
J.Raman Spec., vol. 6, No. 6, 1977, Salares et al.

* cited by examiner

*Primary Examiner*—N. Bhat
(74) *Attorney, Agent, or Firm*—Keil & Weinkauf

(57) ABSTRACT

A process for preparing a stable, aqueous dispersion or a stable water-dispersible dry powder of xanthophylls selected from the group consisting of astaxanthin, lutein and zeaxanthin, by a) dissolving one or more of the abovementioned xanthophylls in a water-miscible organic solvent or a mixture of water and a water-miscible organic solvent at temperatures above 30° C., b) mixing this solution with an aqueous solution of a protective colloid, the solvent component being transferred into the aqueous phase, and the hydrophobic phase of the xanthophyll resulting as nanodisperse phase c) and, where appropriate, converting the dispersion which has formed into a water-dispersible dry powder by removing the solvent and the water and drying, where appropriate in the presence of a coating material, wherein casein or a caseinate is used as protective colloid in step b).

13 Claims, No Drawings

STABLE, AQUEOUS DISPERSIONS AND STABLE, WATER-DISPERSIBLE DRY POWDERS OF XANTHOPHYLLS, AND PRODUCTION AND USE OF THE SAME

Stable aqueous dispersions and stable water-dispersible dry powders of xanthophylls, their preparation and use The invention relates to stable aqueous dispersions and stable water-dispersible dry powders of xanthophylls selected from the group consisting of astaxanthin, lutein and zeaxanthin, and to their preparation and use.

The carotenoid class of substances is classified into two main groups, the carotenes and the xanthopyls. The carotenes which are pure polyene hydrocarbons such as, for example, β-carotene or lycopene differ from the xanthophylls, which also have oxygen functionalities such as hydroxyl, epoxy and/or oxo groups. Typical representatives of this group are astaxanthin, lutein and zeaxanthin, inter alia.

Xanthophylls are widespread in nature and occur inter alia in corn (zeaxanthin), in green beans (lutein), in paprika (capsanthin), in egg yolks (lutein) and in shrimps and salmon (astaxanthin), conferring on these foodstuffs their characteristic color.

These polyenes, which can be both prepared industrially and isolated from natural sources, represent important coloring materials for the human and animal food industries and for the pharmaceutical sector and are, as in the case of astaxanthin, active ingredients with provitamin A activity.

All xanthophylls are insoluble in water, but only low solubility is found in fats and oils. This limited solubility, and the great sensitivity to oxidation, impede direct use of the relatively large-particle synthetic products in the coloring of human and animal foods because only poor coloring results are obtained with the substances in coarsely crystalline form. These disadvantageous effects for practical use of the xanthophylls are particularly evident in aqueous medium.

Only with specifically prepared formulations in which the active ingredients are present in finely dispersed form and, where appropriate, protected from oxidation by protective colloids is it possible to obtain improved color yields in the direct coloring of human foods. In addition, these formulations used in animal feeds result in a higher bioavailability of the xanthophylls and thus indirectly in better coloring properties, for example in egg yolk or fish pigmentation.

Various processes have been described for improving the color yields and for increasing the absorbability and bioavailability, and they all aim at reducing the size of the crystallites of the active ingredients to a range of particle size below 10 μm.

Numerous methods, inter alia described in Chimia 21, 329 (1967), Wo 91/06292 and in WO 94/19411, make use of a colloid mill for grinding the carotenoids and thus achieve particle sizes of from 2 to 10 μm.

A number of combined emulsification/spray drying processes also exist, as described, for example, in DE-A-12 11 911 or in EP-A-0 410 236.

European Patent EP-B-0 065 193 discloses the preparation of finely divided, pulverulent β-carotene preparations by dissolving β-carotene in a volatile, water-miscible organic solvent at temperatures between 50° C. and 200° C., where appropriate under superatmospheric pressure, within a time of less than 10 seconds. The β-carotene is precipitated from the resulting molecularly disperse solution by immediate rapid mixing with an aqueous solution of a protective colloid at temperatures between 0° C. and 50° C. This results in a colloidally dispersed β-carotene hydrosol with an orange-yellow hue. Subsequent spray drying of the dispersion provides a free-flowing dry powder which dissolves in water to form a clear, yellow-orange dispersion.

However, the following phenomena are to be observed with the nanoparticulate active ingredient dispersions of xanthophylls prepared as in EP-B-0 065 193.

The aqueous, xanthophyll-containing active ingredient dispersions are frequently colloidally unstable, especially on concentration. Flocculation of the active ingredient particles, some of which undergo sedimentation and some of which undergo creaming, makes it no longer possible to convert the dispersion into a dry powder.

In the case of xanthophylls with carbonyl functionalities there may also be crosslinking of the gelatin which is employed as the only protective colloid, so that there is formation of a gel which is no longer redispersible and which likewise cannot be converted into a dry powder.

It is thus not always possible to meet the high demands on xanthophyll-containing formulations in relation to coloring effect and bioavailability because of the problems described with the abovementioned process.

As described in WO 98/26008, the redispersibility of the xanthophyll-containing dry powders can be improved by using a mixture of low molecular and high molecular weight protective colloids.

It is an object of the present invention to propose a process for preparing a stable aqueous dispersion of xanthophylls selected from the group consisting of astaxanthin, lutein and zeaxanthin. It is further intended to provide stable pulverulent preparations of the abovementioned xanthophylls with which a good coloring effect and moreover high bioavailability can be achieved.

We have found that this object is achieved by a process for preparing a stable, aqueous dispersion or a stable water-dispersible dry powder of xanthophylls selected from the group consisting of astaxanthin, lutein and zeaxanthin, by a) dissolving one or more of the xanthophylls selected from the group consisting of astaxanthin, lutein and zeaxanthin in a water-miscible organic solvent or a mixture of water and a water-miscible organic solvent at temperatures above 30° C., b) mixing this solution with an aqueous solution of a protective colloid, the solvent component being transferred into the aqueous phase, and the hydrophobic phase of the xanthophyll resulting as nanodisperse phase c) and, where appropriate, converting the dispersion which has formed into a water-dispersible dry powder by removing the solvent and the water and drying, where appropriate in the presence of a coating material, wherein casein or a caseinate is used as protective colloid in step b).

The preparations according to the invention are generally prepared by dissolving at least one of the above-mentioned xanthophylls, where appropriate together with an edible oil, in a water-miscible organic solvent at temperatures above 30° C., preferably between 50° C. and 240° C., in particular 100° C. to 200° C., particularly preferably 140° C. to 180° C., where appropriate under pressure.

Since the exposure to high temperatures may reduce the desired high all-trans isomer content, the xanthophyll(s) is/are dissolved as quickly as possible, for example in the region of seconds, for example in 0.1 to 10 seconds, particularly preferably in less than 1 second. For rapid preparation of the molecularly disperse solution, the application of elevated pressure, for example in the range from 20 bar to 80 bar, preferably 30 to 60 bar, may be advantageous.

Immediately thereafter, the optionally cooled aqueous solution of the casein or caseinate is added to the molecularly disperse solution obtained in this way, preferably so that a mixing temperature of about 35° C. to 80° C. is set.

During this, the solvent component is transferred into the aqueous phase, and the hydrophobic phase of the xanthophyll(s) results as nanodisperse phase.

For a detailed description of the process and apparatus, express reference is made at this point to EP-B-0 065 193.

The protective colloids used are low and/or high molecular weight casein or caseinate or mixtures thereof. Na caseinate with a molecular weight of from 10,000 to 100,000 is preferably used, particularly preferably with an MW of from 20,000 to 60,000, for example Na caseinate supplied by Lacto Bretagne Associés S.A. (France) with an MW of about 38,000.

Details of the casein/caseinate employed are to be found, inter alia, in Ullmann's Encyclopedia of Industrial Chemistry, 6th Edition, 1998 Electronic Release, Chapter 11.1., Wiley-VCH, Weinheim, Germany and in CD Römpp Chemie Lexikon-Version 1.0, Stuttgart/New York: Georg Thieme Verlag 1995 and the literature cited therein.

To increase the mechanical stability of the final product, it is expedient to add to the colloid a plasticizer such as sugars or sugar alcohols, for example sucrose, glucose, lactose, invert sugar, sorbitol, mannitol or glycerol.

The ratio of protective colloid and plasticizer to xanthophyll solution is generally chosen so that the final product contains between 0.5 and 30% by weight, preferably 5 to 25% by weight, particularly preferably 10 to 23% by weight of xanthophyll, 10 to 70% by weight of a protective colloid, 10 to 70% by weight of a plasticizer, all percentage data based on the dry weight of the powder, and, where appropriate, small amounts of a stabilizer.

The xanthophylls which can be employed for carrying out the invention are the known natural or synthetic compounds astaxanthin, lutein and/or zeaxanthin. Astaxanthin should be mentioned as the xanthophyll preferably employed for the process according to the invention.

To increase the stability of the active ingredient against oxidative degradation, it is advantageous to use stabilizers such as α-tocopherol, t-butylhydroxytoluene, t-butylhydroxyanisole, ascorbic acid or ethoxyquin. They can be added either to the aqueous or to the solvent phase, but they are preferably dissolved together with the xanthophylls in the solvent phase.

It may also be advantageous in some circumstances additionally to dissolve in the solvent phase a physiologically approved oil such as, for example, sesame oil, corn oil, cottonseed oil, soybean oil or arachis oil, and esters of medium chain-linked vegetable fatty acids in a concentration of from 0 to 500% by weight, preferably 10 to 300% by weight, particularly preferably 20 to 100% by weight, based on the xanthophyll(s), which is then precipitated in extremely fine-particle form together with the active ingredients and the additives mentioned on mixing with the aqueous phase.

It is surprisingly possible on use according to the invention of casein or caseinate as protective colloid to dispense with the use of additional emulsifiers such as, for example, ascorbyl palmitate.

It has also been found that colloidally stable and non-crosslinking nanoparticulate active ingredient dispersions of xanthophylls whose viscosity behavior approximately corresponds to that of newtonian fluids are obtained. Fluids of this type are distinguished by their flow resistance, defined by Newton's equation $\tau = h \cdot D$, which is a material constant at a given temperature ($\tau$=yield stress, D=shear gradient, h=dynamic viscosity). Graphical representation of the flow behavior of newtonian fluids gives approximately a straight line at a given temperature. In particular, the viscosity of the active ingredient dispersion changes by less than ±50% in the shear range between $10^{-2}$ sec$^{-1}$ and $10^{+2}$ sec$^{-1}$ at 40° C. and at 60° C.

The advantages of this approximately newtonian viscosity behavior are, inter alia, that the active ingredient dispersions can be pumped more easily, especially after concentration, than is the case with dispersions with structural viscosity. In spray drying, in addition, the approximately newtonian active ingredient dispersions have the advantage that the parameters of the spray head can be optimized more easily and that these dispersions behave less critically in the spray head.

It has also been observed that the formation of H aggregates of xanthophylls is avoided in the process.

The aggregation of carotenoids is a phenomenon which has been disclosed in the literature and is described in numerous publications [P. Song, T. A. Moore, Photochemistry and Photobiology, 19, 435–441 (1974); A. V. Ruban, P. Horton, A. J. Young, J. Photochem. Photobiol. B: Biol., 21, 229–234 (1993); V. R. Salares, N. M. Young, P. R. Carey, H. J. Bernstein, Journal of Raman Spectroscopy, 6(6), 282–288 (1977)].

Carotenoid aggregates may, for example, be produced by mixing a solution of a carotenoid in a water-miscible organic solvent such as, for example, isopropanol, ethanol, acetone or tetrahydrofuran with water.

It is thus possible, as described in the above-mentioned literature, to produce either so-called H or J aggregates on choice of the correct ratios of amounts of water and organic solvent.

H aggregates mean that the polyene chains are stacked like a pack of cards (card-stack aggregate), which can be characterized in the UV/Vis spectrum by the appearance of a new band showing a hypsochromic shift compared with the absorption of the monomer forms, in the range between 320 and 400 nm. J aggregates by contrast represent either a linear head-tail linkage (head-tail aggregates) of the polyenes, or they are arranged like fish bones (herringbone aggregates). Both arrangements cause a bathochromic shift in the UV absorption of the polyenes.

Feeding tests on trout have shown that H aggregates of xanthophylls, especially the H aggregates of astaxanthin, show a bioavailability which is worse than that of the corresponding J aggregates, which represents a further advantage of the dispersions and dry powders prepared by the process according to the invention.

A deep-colored viscous liquid is obtained depending on the amount of casein or caseinate used. Removal of the solvent can take place, for example, by extraction with a water-immiscible solvent, or, depending on the boiling point in a manner known per se, for example by distillation, where appropriate under reduced pressure. In this case, it has proven expedient and possible to employ the azeotrope obtained on use of isopropanol without removing water directly as solvent. However, the removal of solvent preferably takes place together with the removal of water by spray drying or spray granulation.

The invention thus also relates to stable aqueous dispersions and stable water-dispersible dry powders of xanthophylls from the group consisting of astaxanthin, lutein and zeaxanthin which are obtainable by the process described above.

A stable dry powder is obtained and is enveloped by a casein, caseinate or mixtures thereof as protective colloid. This dry powder can be redissolved in water to obtain a uniform fine distribution of the active ingredient in the particle size range below 1 μm. The active ingredient hydrosol obtained in this way proves, despite the fine dispersion, to be extremely stable in a photochemical stability test.

The active ingredient present both in the aqueous xanthophyll dispersion and in the dry powder prepared therefrom shows an amorphous content, determined from X-ray diffraction diagrams, between 70 and 100%, preferably between 90 and 100%. In addition, the all-trans isomer content of the xanthophylls is at least 50%, preferably 70%.

The preparations according to the invention are outstandingly suitable as human and animal food coloring matter and as addition to pharmaceuticals. Examples of typical areas of use in the animal feed sector are fish pigmentation in aquaculture and egg yolk and broiler skin pigmentation in poultry rearing.

The procedure for the process according to the invention is explained in detail in the following example.

EXAMPLE 1

40 g of astaxanthin were suspended in 294 g of isopropanol/water (88/12, w/w) at a temperature of 30° C. in a heatable receiver. This suspension was mixed in a mixing chamber at a mixing temperature of 170° C. with 536 g of isopropanol/water (88/12, w/w) with a residence time of 0.2 seconds. Immediately after the stated residence time, the resulting molecularly dispersed astaxanthin solution entered another mixing chamber in which 10.4 kg of an aqueous Na caseinate solution which, besides 108 g of caseinate contained 36 g of sucrose and had been adjusted to pH 9 were admixed at a mixing angle of 90° C. through a high-pressure pump, the astaxanthin precipitating in colloidally dispersed form with an average particle size of 144 nm at a temperature of 45° C.

The dispersion was then concentrated and converted in a manner known per se into a free-flowing 22% strength astaxanthin dry powder with an average particle size of 129 nm. The dry powder dissolved in water once again to form a clear red dispersion, the color strength of the redispersion being only about 10% less than that of the original dispersion.

We claim:

1. A process for preparing a stable, aqueous dispersion or a stable water-dispersible dry powder of xanthophylls selected from the group consisting of astaxanthin, lutein and zeaxanthin, by a) dissolving one or more of the xanthophylls selected from the group consisting of astaxanthin, lutein and zeaxanthin in a water-miscible organic solvent or a mixture of water and a water-miscible organic solvent at temperatures above 30° C., b) mixing this solution with an aqueous solution of a protective colloid, the solvent component being transferred in to the aqueous phase, and the hydrophobic phase of the xanthophyll resulting as nanodisperse phase c) and, where appropriate, converting the dispersion which has formed into a water-dispersible dry powder by removing the solvent and the water and drying, where appropriate in the presence of a coating material, wherein casein or a caseinate is used as protective colloid in step b).

2. A process as claimed in claim 1, wherein an edible oil is used in addition to the xanthophyll in step a).

3. A process as claimed in claim 1, wherein no additional emulsifier is used.

4. A process as claimed in claim 1, wherein the formation of H aggregates of the xanthophylls is avoided.

5. A process as claimed in claim 1, wherein astaxanthin is used as xanthophyll.

6. A stable aqueous dispersion of xanthophylls selected from the group consisting of astaxanthin, lutein and zeaxanthin, obtainable by a process as defined in claim 1.

7. A stable aqueous dispersion of xanthophylls as claimed in claim 6, wherein the xanthophyll present has an amorphous content between 70 and 100%.

8. A stable aqueous dispersion of xanthophylls as claimed in claim 6, wherein the xanthophyll present has an all-trans isomer content of at least 50%.

9. A stable aqueous dispersion of xanthophylls as claimed in claim 6, which shows the viscosity behavior of newtonian fluids.

10. A stable aqueous dispersion of xanthophylls as claimed in claim 6, which is a dispersion of astaxanthin.

11. A stable water-dispersible dry powder of xanthophylls selected from the group consisting of astaxanthin, lutein and zeaxanthin, obtainable by a process as defined in claim 1.

12. A stable water-dispersible dry powder of xanthophylls as claimed in claim 11, which is a dry powder of astaxanthin.

13. Human foods, pharmaceuticals and/or animal feeds comprising the stable aqueous dispersions and/or stable water-dispersible dry powders of xanthphylls defined in claim 6.

* * * * *